United States Patent [19]

Cooper et al.

[11] 4,230,724

[45] Oct. 28, 1980

[54] METHOD OF TREATING VASCULARIZATION OF THE EYE WITH FLURBIPROFEN

[75] Inventors: Charles A. Cooper; Michael V. W. Bergamini, both of Irvine, Calif.

[73] Assignee: Allergan Pharmaceuticals, Inc., Irvine, Calif.

[21] Appl. No.: 57,608

[22] Filed: Jul. 16, 1979

[51] Int. Cl.³ .............................................. A61K 31/19
[52] U.S. Cl. .................................................... 424/317
[58] Field of Search ......................................... 424/317

[56] References Cited

U.S. PATENT DOCUMENTS

| | | | |
|---|---|---|---|
| 3,755,427 | 8/1973 | Adams et al. | 424/317 |
| 3,793,457 | 2/1974 | Adams et al. | 424/317 |
| 3,865,949 | 2/1975 | Greig | 424/317 |
| 4,009,283 | 2/1977 | Herr et al. | 424/317 |

OTHER PUBLICATIONS

The Merck Index-9th ed. (1976), item 2514.

*Primary Examiner*—Douglas W. Robinson
*Attorney, Agent, or Firm*—Martin A. Voet

[57] ABSTRACT

A method of treating vascularization of the eye as a result of traumatic injury, surgery, such as, corneal transplant, or onset of diabetic retinopathy by topically treating the eye with Flurbiprofen or a pharmaceutically acceptable salt thereof.

9 Claims, No Drawings

METHOD OF TREATING VASCULARIZATION OF THE EYE WITH FLURBIPROFEN

BACKGROUND OF THE INVENTION

1. Field of the Invention

The invention relates to a method of treating vascularization of the eye. More specifically, the invention relates to a method for preventing or inhibiting corneal vascularization resulting from trauma or disease.

2. Background of the Prior Art

The normally avascular cornea may be invaded by blood vessels in pathological states primarily as a defense mechanism against disease or injury. This action is generally known as "corneal vascularization" or "neovascularization." For purposes of this invention disclosure, the terms "vascularization" will be used to refer to the foregoing phenomenon. While vascularization may have some benefit to the traumatized tissue in reducing inflammation and the like, there is a substantial risk of loss of transparency of the cornea as a result of excessive vascularization and vascularization is permanent. In addition, in vascularization of the iris, the new blood vessels may cover the trabecular meshwork, cause peripheral anterior synechiae, and give rise to an intractable angle-closure type of glaucoma.

The cause of corneal vascularization is unknown, though numerous theories have been suggested. Clinically, corneal vascularization is characterized initially by an engorgement of the perilimbal plexus and then by an invasion of the cornea itself by vessels of new formation.

Prior art treatment of corneal vascularization includes topical use of corticosteroids, such as, cortisone and prednisolone acetate, irradiation and surgery.

Flurbiprofen and its pharmaceutically acceptable salts are known in the prior art, are commercially available, and are fully described in U.S. Pat. No. 3,793,457 and U.S. Pat. No. 3,755,427 as anti-inflammatory agents.

SUMMARY OF THE INVENTION

The invention relates to a method of treating trauma-induced vascularization of the cornea comprising topically administering to the eye an effective, vascularization-inhibiting amount of Flurbiprofen or a pharmaceutically acceptable salt thereof.

The invention further relates to a method of treating surgically-induced vascularization of the cornea following corneal transplant comprising topically administering to the eye an effective, vascularization-inhibiting amount of Flurbiprofen or a pharmaceutically acceptable salt thereof.

In addition the invention relates to a method of treating diabetic retinopathy in humans comprising topically administering to the eye an effective, diabetic retinopathy-inhibiting amount of Flurbiprofen or a pharmaceutically acceptable salt thereof.

DESCRIPTION OF THE INVENTION

Suitable ophthalmic carries are known to those skilled in the art and all such conventional carriers may be employed in the present invention. Thus, a particular carrier may take the form of a sterile, ophthalmic ointment, cream, gel, solution, or dispersion. Also included in suitable ophthalmic carries are slow release polymers, e.g., "Ocusert" polymers, "Hydron" polymers, etc. Stabilizers may also be used such as, for example, chelating agents, e.g., EDTA. Antioxidants may also be used, e.g., sodium bisulfite, sodium thiosulfite, 8-hydroxy quinoline or ascorbic acid. Sterility typically will be maintained by conventional ophthalmic preservatives, e.g., chlorbutanol, benzalkonium chloride, cetypyridium chloride, phenyl mercuric salts, thimerosal, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carries are preferred. Solutions may be manually delivered to the eye in suitable dosage form, e.g., eye drops, or delivered by suitable microdrop or spray apparatus typically affording a metered dose of medicament. Examples of suitable ophthalmic carriers include sterile, substantially isotonic, aqueous solutions containing minor amounts, i.e., less than about 5% by weight hydroxypropylmethylcellulose, polyvinyl alcohol, carboxymethylcellulose, hydroxyethylcellulose, glycerine and EDTA. The solutions are preferably maintained at substantially neutral pH and isotonic with appropriate amounts of conventional buffers, e.g., phosphate, borate, acetate, tris, etc.

A preferred ophthalmic composition is a preserved aqueous solution containing the following ingredients at the indicated concentration.

| | | |
|---|---|---|
| Flurbiprofen | Wt. percent | 0.03 |
| Stabilizer | Wt. percent | 0.01 |
| Preservative | Wt. percent | 0.005 |
| Buffer | M | 0.05 |
| NaCl q.s. ad isotonic | | |
| Water q.s. ad 100 percent. | | |

The amount of Flurbiprofen to be used will vary with the severity of the vascularization. Generally a dose level of one or two drops of the foregoing aqueous solution 1–4 times daily would be a suitable dosage amount. Generally, the concentration of Flurbiprofen will vary between about 0.005 and about 2 and preferably between about 0.03 and 1%.

The term "treating" as used in this disclosure refers to a range of activity from preventing the onset or occurrence of vascularization to inhibiting its progression. That is, in certain cases, the treatment might successfully substantially prevent the onset of the condition while in other cases the treatment would instead reduce the severity of the condition.

EXAMPLE

MATERIALS AND METHODS

Silver Nitrate Cauterization

Using the technique of Fromer and Klintworth*, silver nitrate burns were applied to initiate the neovascular stimulus. New Zealand albino rabbits weighting 2–3 kg were sedated with intramuscular ketamine HCl, and given one drop Proparacaine HCl topically in both eyes. After a few seconds, the excess anesthetic was washed out with distilled water to prevent silver chloride precipitation. An AgNO$_3$ applicator stick (Graham-Field, New Hyde Park, NY) was touched to the cornea with slight pressure for 5–7 seconds, three millimeters from the corneal-scleral limbus at 12 o'clock. The position and duration of the burn selected provided a stimulus that produced vessel growth in most cases, but was not so strong as to mask any therapeutic effect of the medications. Within 30 minutes after the burn was applied, the medication to be used was started: one drop four times per day. Three groups of rabbits were used and were treated with 1% Prednisolone acetate, 0.01% Sodium flurbiprofen, or 0.1% Sodium Flurbiprofen in conventional ophthalmic vehicles. The other eye received a vehicle control following the burn. All eyes were examined by slit-lamp biomicroscopy daily for seven days. They were assessed for length of the leading vessel in the neovascular tuft using a measuring reticle, and vessels on the cornea were measured and counted to get an idea of total length of vessels invading the cornea.

*Fromer, Carl H. and Klintworth, Gordon K.: "An Evaluation of the Role of Leukocytes in the Pathogenesis of Experimentally Induced Corneal Vascularization," Am. J. Pathol. 79:537, 1975.

RESULTS

AgNO$_3$ Technique—In controls, vessels were usually seen invading the cornea by Day 2 or Day 3, and continued in toward the burn during subsequent days. Six animals in the Prednisolone Test Group did not show any vascular invasion in either control or experimental eye, and were not included in the data analysis. Values for degree of corneal invasion in the various experiments are listed in the Table. Prednisolone did not significantly alter vascularization. However, 0.1% Flurbiprofen decreased vessel proliferation and delayed its onset. By Day 7, the mean total length of vessels present on the vehicle control group was five times that present in the 0.1% Flurbiprofen group (30 mm vs. 6 mm). This difference is highly significant (p<0.005). Results with 0.01% Flurbiprofen were less dramatic, but nonetheless, demonstrated a substantial decrease in the amount and rate of vessel growth.

TABLE

RESULTS OF EXPERIMENTS USING AgNO$_3$ CAUTERIZATION*

| Days After Burn | Flurbiprofen Vehicle Control (n = 32) | 0.1% Flurbiprofen (n = 14) | 0.01% Flurbiprofen (n = 18) |
|---|---|---|---|
| | mm | mm | mm |
| 1 | 0 | 0 | 0 |
| 2 | 0.03 ± 0.02/0.2 ± 0.1 | 0.01 ± 0.01/0.03 ± 0.03 | 0 |
| 3 | 0.2 ± 0.04/8 ± 3 | 0.17 ± 0.1/1.4 ± 0.7 | 0.13 ± 0.04/1.5 ± 0.5 |
| 4 | 0.8 ± 0.1/18 ± 5 | 0.3 ± 0.1/2 ± 0.8 | 0.5 ± 0.1/7 ± 2 |
| 5 | 1.0 ± 0.1/24 ± 6 | 0.6 ± 0.1/5 ± 1.4 | 0.7 ± 0.1/10 ± 3 |
| 6 | 1.3 ± 0.1/28 ± 7 | 0.7 ± 0.1/6 ± 1.4 | 0.9 ± 0.1/14 ± 3 |
| 7 | 1.3 ± 0.1/30 ± 7 | 0.8 ± 0.1/6 ± 1.4 | 1.0 ± 0.1/16 ± 4 |

| Days After Burn | Prednisolone Vehicle Control (n = 11) | 1% Prednisolone Acetate (n = 11) |
|---|---|---|
| | mm | mm |
| 1 | 0 | 0 |
| 2 | 0 | 0 |
| 3 | 0.3 ± 0.1/2.7 ± 0.9 | 0.2 ± 0.03/0.7 ± 0.2 |
| 4 | 1.0 ± 0.1/10 ± 2 | 0.8 ± 0.1/9 ± 2 |
| 5 | 1.2 ± 0.1/17 ± 3 | 1.1 ± 0.1/14 ± 2 |
| 6 | 1.3 ± 0.1/22 ± 4 | 1.2 ± 0.1/18 ± 3 |
| 7 | 1.3 ± 0.1/26 ± 5 | 1.3 ± 0.1/23 ± 5 |

*Expresses as A ± S.E./B ± S.E., where A represents length of leading vessel (means of all experiments), and B represents total length of all vessels on cornea (mean of all experiments). Units in mm.

We claim:

1. A method of treating trauma-induced vascularization of the cornea comprising topically administering to the eye an effective, vascularization-inhibiting amount of Flurbiprofen or a pharmaceutically acceptable salt thereof.

2. The method of claim 1 wherein the amount of Flurbiprofen ranges between about 0.005 and about 2%.

3. The method of claim 1 wherein the amount of Flurbiprofen ranges between about 0.03 and 1%.

4. A method of treating surgically-induced vascularization of the cornea following corneal transplant comprising topically administering to the eye an effective, vascularization-inhibiting amount of Flurbiprofen or a pharmaceutically acceptable salt thereof.

5. The method of claim 4 wherein the amount of Flurbiprofen ranges between about 0.005 and about 2%.

6. The method of claim 4 wherein the amount of Flurbiprofen ranges between about 0.03 and 1%.

7. A method of treating diabetic retinopathy in humans comprising topically administering to the eye an effective, diabetic retinopathy-inhibiting amount of Flurbiprofen or a pharamaceutically acceptable salt thereof.

8. The method of claim 7 wherein the amount of Flurbiprofen ranges between about 0.005 and about 2%.

9. The method of claim 7 wherein the amount of Flurbiprofen ranges between about 0.03 and 1%.

* * * * *

UNITED STATES PATENT AND TRADEMARK OFFICE
CERTIFICATE OF CORRECTION

PATENT NO. : 4,230,724

DATED : October 28, 1980

INVENTOR(S) : Charles A. Cooper; Michael V. W. Bergamini

It is certified that error appears in the above—identified patent and that said Letters Patent is hereby corrected as shown below:

At Column 1, Line 60 and Column 2, Line 12, the word "carries" should be - carriers -

Signed and Sealed this

Nineteenth Day of May 1981

[SEAL]

Attest:

RENE D. TEGTMEYER

Attesting Officer

Acting Commissioner of Patents and Trademarks